US006452067B1

(12) United States Patent
Bedbrook et al.

(10) Patent No.: US 6,452,067 B1
(45) Date of Patent: Sep. 17, 2002

(54) METHODS TO ASSAY FOR POST-TRANSCRIPTIONAL SUPPRESSION OF GENE EXPRESSION

(75) Inventors: John R. Bedbrook, Piedmont; Neal Gutterson, Oakland; Paul W. Oeller, Berkley, all of CA (US)

(73) Assignee: DNA Plant Technology Corporation, Oakland, CA (US)

( * ) Notice: Subject to any disclaimer, the term of this patent is extended or adjusted under 35 U.S.C. 154(b) by 0 days.

(21) Appl. No.: 09/156,210

(22) Filed: Sep. 17, 1998

Related U.S. Application Data
(60) Provisional application No. 60/059,332, filed on Sep. 19, 1997.

(51) Int. Cl.[7] .......................... C12N 15/82; C12N 15/84; C12N 15/90; C12N 5/04; A01H 5/00
(52) U.S. Cl. ...................... 800/278; 435/69.7; 435/468; 800/280; 800/286; 800/288; 800/294
(58) Field of Search ................................. 435/69.1, 410, 435/419, 468, 469, 98.7; 800/278, 279, 280, 285, 286, 288, 294, 295, 298

(56) References Cited

U.S. PATENT DOCUMENTS

| | | | |
|---|---|---|---|
| 5,034,323 A | 7/1991 | Jorgensen et al. | 435/468 |
| 5,231,020 A | 7/1993 | Jorgensen et al. | 800/278 |
| 5,283,184 A | 2/1994 | Jorgensen et al. | 435/468 |
| 5,316,930 A | 5/1994 | Loesch-Fries et al. | 435/468 |
| 5,453,566 A | 9/1995 | Shewmaker et al. | 800/278 |
| 5,457,281 A | 10/1995 | Bridges et al. | 800/278 |

OTHER PUBLICATIONS

Angell, et al., "Consistent Gene Silencing In Transgenic Plants Expressing A Replicating Potato Virus X RNA,"60 *The Embo Journal*, vol. 16, No. 12, pp. 3675–3684, (1997).
Baulcombe, "RNA As A Target And An Initiator Of Post–Transcriptional Gene Silencing In Trangenic Plants," *Plant Molecular Biology*, pp. 79–88, (1996).
Diekman, et al., *The EMBO Journal*, vol. 7, pp. 3315–3320 (1988).
Diekman, et al., *Plant Physiol.* vol. 100, pp. 2013–2017 (1992)).
Elmayan, et al., "Expression of Single Copies of a Strongly Expressed 35S Transgene Can Be Silenced Post–Transcriptionally," *The Plant Journal*, 9(6). pp. 787–797. (1966).
English, et al., *Plant Cell*, vol. 9, pp. 179–188 (1996).
Fullner, et al., "Temperature Affects the T–DNA Transfer Machinery of *Agrobacterium Tumefaciens*," *Journal of Bacteriology*, pp. 1498–1504. (Mar. 1996).
Goodwin, et al., "Genetic and Biochemical Dissection of Transgenic RNA–Mediated Virus Resistance," *The Plant Cell*, vol. 8, pp. 95–105, (Jan. 1996).
Harpster, et al., *Plant Mol. Biol.*, vol. 33, pp. 45–57, (1997).
Jefferson, et al., *Proc. National Academy Science USA*, vol. 83, p. 8447, (1986).
Jefferson, et al., *Plant Mol. Biol, Reporter*, vol. 5, p.387, (1987).
Lincoln, et al., *Proc. National Academy Science USA*,vol. 84, pp. 2793–2797, (1988).
Mueller, et al., "Homology–Dependent Resistance: Transgenic Virus Resistance in Plants Related to Homology–Dependent Gene Silencing," *The Plant Journal*, vol. 7, pp. 1001–1013, (1995).
Ni, et al., *The Plant Journal*, vol. 7, pp. 661–676, (1995).
Vancanneyt, et al., "Construction of an Intron–Containing marker Gene: Splicing of the Intron in Transgenic Plants and its use in Monitoring Early Events in Agrobacterium–Mediated Plant Transfomation," *Mol Gen Genet* 220:pp. 245–250, (1990).
Smith, et al., Transgenic Plant Virus Resistance Medicated By Untranslatable Sense RNAs: Expression, Regulation, and Fate of Nonessential RNSs, *The Plant Cell*, vol.6, pp. 1441–1453, (Oct. 1994).
Stam, et al., "The Silence of Genes in Transgenic Plants," *Annals of Botany*, vol. 79, pp. 3–12, (1990).

*Primary Examiner*—Amy J. Nelson
*Assistant Examiner*—Ashwin Mehta
(74) *Attorney, Agent, or Firm*—Townsend and Townsend and Crew LLP

(57) ABSTRACT

This invention provides methods for identifying plant cells that exhibit post-transcriptional gene silencing (PTGS) of a chosen gene. The methods involve the use of suppression-sensitive reporter genes that, when introduced into plant cells, are expressed at a lower level in cells that exhibit PTGS than in cells that are not silenced for the particular gene.

32 Claims, 1 Drawing Sheet

METHODS TO ASSAY FOR POST-TRANSCRIPTIONAL SUPPRESSION OF GENE EXPRESSION

CROSS-REFERENCE TO RELATED APPLICATIONS

This application claims benefit of U.S. provisional application Ser. No. 60/059,332, filed Sep. 19, 1997, which application is incorporated herein by reference for all purposes.

BACKGROUND OF THE INVENTION

1. Field of the Invention

This invention pertains to the use of recombinant DNA methods to screen plants previously transformed with exogenous nucleic acids to determine whether the plants exhibit post-transcriptional gene silencing. More particularly, the invention relates to a rapid, simple method for screening large populations of transgenic plants, as well as for quantitating extent of suppression.

2. Background

Introduction of transgenes into plants can result in reduced expression of endogenous genes. Many plants exhibit such reduced expression as a result of post-transcriptional reduction of gene expression, a phenomenon that is referred to as post-transcriptional gene silencing (PTGS; for review, see, e.g., Baulcombe (1996) *Plant Mol. Biol.* 32: 79–88; Stam et al. (1997) *Annals of Botany* 79: 3–12). PTGS has been reported to involve degradation of nucleic acids that are related to the introduced transgene sequence. For example, the transcriptional rate of the endogenous gene is not altered in plants exhibiting sense suppression of that gene, but the accumulation of the mature mRNA for the endogenous gene is reduced. Elmayan and Vaucheret (1996) Plant J. 9: 787–797.

PTGS can have various effects. If one is attempting to obtain high level expression of a transgene, for example, PTGS of the transgene is counterproductive because it results in decreased expression of the transgene. Often, however, PTGS provides a convenient mechanism for altering the phenotype of a plant by reducing or eliminating the expression of a particular endogenous gene or transgene. PTGS can also mediate plant resistance to infection by viruses. Introduction of a transgene derived from a plant virus can induce post-transcriptional silencing of the corresponding gene of subsequently introduced virus, which can prevent establishment of viral infection. See, e.g., English et al. (1996) *Plant Cell* 8: 179–188.

The frequency with which post-transcriptional gene silencing is obtained in a population of plants, each of which is the result of an independent transformation event, can range widely, from less than 1% to 30% or more. A screening step is therefore useful in the production of plants which exhibit post-transcriptional gene silencing. Several screening methods have been used to select from a transgenic plant population those plants in which expression of a targeted gene is suppressed. These screening methods include:

1) Visual screening of a suitable trait (e.g., flower color);
2) Quantitation of the final product of a biosynthetic pathway that includes the protein product of the targeted gene as a pathway enzyme;
3) Quantitation of the protein product of the target gene;
4) Quantitation of the mRNA product of the target gene, using Northern analysis, RNase protection assay, RT-PCR, or other suitable technique;
5) Quantitation of the transgene mRNA in vegetative tissue using Northern analysis or other suitable technique.

Such methods have been used to screen transgenic populations for both anti-sense suppression and sense-mediated suppression. The first four of the above screening procedures require that the appropriate tissue of the mature plant is produced, and that extracts of the plant tissue are made for analysis. A significant drawback to these methods is that an appropriate tissue is sometimes produced only after an extended period of plant development, e.g., in flowers or fruit. In addition, the screening methods require one to prepare tissue extracts and perform complex molecular or biochemical analysis. The fifth screening method, quantitation of transgene mRNA in vegetative tissue, also has significant drawbacks. Theoretically, plants that exhibit only a small amount of transgene message in leaf tissue would be candidates for suppression of the endogenous gene. However, post-transcriptional silencing is but one of several mechanisms that could account for poor transgene expression. For example, poor transgene expression can result from insertion of the transgene in a transcriptionally inactive region of the genome.

Thus, a need exists for improved methods to screen for post-transcriptional silencing of gene expression. Preferably, these screening protocols would be suitable for analysis of young plants and plant tissues, and would not require complex procedures. Also needed are assays that can distinguish post-transcriptional silencing and other causes of poor transgene expression. The present invention fulfills these and other needs.

SUMMARY OF THE INVENTION

In a first embodiment, the invention provides a method for detecting post-transcriptional gene silencing (PTGS) in a plant cell. The method involves introducing into the plant cell a nucleic acid comprising a promoter operably linked to a suppression-sensitive reporter (SSR) gene which comprises a) a reporter coding sequence, and b) a targeting nucleotide sequence. The targeting nucleotide sequence is at least substantially identical to a region of a chosen gene. The reporter coding sequence and the targeting nucleotide sequence are transcribed as a single mRNA transcript. The level of expression of the SSR gene is determined to ascertain whether post-transcriptional gene silencing has occurred.

The invention also provides a method for detecting PTGS that involves, in addition to the use of an SSR gene, introducing into the plant cell a non-suppression sensitive reporter (NSR) gene. The NSR gene has a second reporter coding sequence which is different from the reporter coding sequence included in the SSR gene, and lacks a targeting nucleotide sequence. The level of expression of both the SSR gene and the NSR gene are determined. By comparing the expression levels, one can quantitate the degree of PTGS.

In another embodiment, the invention provides methods for detecting transgene-induced post-transcriptional silencing of a transgene in a plant cell by introducing into the plant cell a nucleic acid comprising a promoter operably linked to a suppression-sensitive reporter (SSR) gene which comprises a) a reporter coding sequence, and b) a targeting nucleotide sequence. The targeting nucleotide sequence is substantially identical to a region of the transgene, and is transcribed as a single mRNA transcript with the reporter coding sequence. The level of expression of the SSR gene is determined to ascertain whether post-transcriptional suppression has occurred.

A method for detecting transgene-induced post-transcriptional silencing of an endogerious gene in a plant cell is also provided by the invention. The method involves the steps of: 1) introducing into the plant cell a nucleic acid comprising a promoter operably linked to a suppression-sensitive reporter (SSR) gene which comprises a) a reporter coding sequence, and b) a targeting nucleotide sequence that is substantially identical to a region of the endogenous gene, wherein the reporter coding sequence and the targeting nucleotide sequence are transcribed as a single mRNA transcript; and 2) determining the level of expression of the SSR gene to determine whether post-transcriptional suppression has occurred.

The invention also provides methods for assaying a plant to determine whether a chosen gene is post-transcriptionally silenced. These methods involve introducing into cells obtained from the plant a nucleic acid comprising a promoter operably linked to a suppression-sensitive reporter (SSR) gene which comprises a) a reporter coding sequence, and b) a targeting nucleotide sequence that is substantially identical to a region of the chosen gene. The reporter coding sequence and the targeting nucleotide sequence are transcribed as a single mRNA transcript. A decrease in the level of expression of the SSR gene is indicative of post-transcriptional gene silencing.

Methods of identifying plant cells that are resistant to infection by a plant virus are also provided. These methods involve the steps of: 1) introducing into the plant cells a nucleic acid comprising a promoter operably linked to a suppression-sensitive reporter (SSR) gene which comprises a) a reporter coding sequence, and b) a targeting nucleotide sequence wherein such targeting nucleotide sequence is substantially identical to a region of a nucleotide sequence obtained from a plant virus, wherein the reporter coding sequence and the targeting nucleotide sequence are transcribed as a single mRNA transcript; and 2) determining the level of expression of the SSR gene. A reduction in SSR gene expression is indicative of cells that are resistant to infection by the plant virus.

The invention also provides plants in which expression of a chosen gene is post-transcriptionally suppressed, and parts obtained from such plants. The plants are obtained by culturing plant cells which have been determined to exhibit post-transcriptional suppression of the chosen gene by determining the level of expression of a suppression-sensitive reporter (SSR) gene which comprises a) a reporter coding sequence, and b) a targeting nucleotide sequence that is substantially identical to the chosen gene, wherein the reporter coding sequence and the targeting nucleotide sequence are transcribed as a single mRNA transcript. These plants can also include a transgene that is substantially identical to, or capable of specifically hybridizing to, the chosen gene.

DETAILED DESCRIPTION

Definitions

Figure 1:
FIG. 1 shows a schematic diagram of a typical suppression-sensitive reporter cassette.

As used herein, "homologous" means corresponding to (the same as). For example, an RNA which is homologous to a gene will be substantially identical to, or correspond to, the coding strand sequence (with the normal exception of uracil for RNA in place of thymidine for DNA). Thus, cellularly produced "homologous mRNA", as used herein, is complementary to the template DNA strand of the gene.

RNA resulting from transcription is referred to herein on occasion as a "transcript" or in some instances "mRNA". Typically, "mRNA" or "messenger" refers to a transcript which is processed (e.g., introns removed and 3' end polyadenylated). mRNA may contain "coding regions" of codon triplets which encode for translation into amino acids making up a polypeptide. A primary transcript may contain both exons (typically containing the coding regions) and introns, the latter of which are often excised prior to translation.

A "heterologous" sequence is one that originates from a foreign species, or, if from the same species, is substantially modified from its original form.

As used herein, "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "regeneration" as used herein, means growing a whole plant from a plant cell, a group of plant cells, a plant part or a plant piece (e.g. from a protoplast, callus, or tissue part).

As used herein, the term "transformation" means alteration of the genotype of a host plant by the introduction of a nucleic acid sequence. The nucleic acid sequence need not necessarily originate from a different source, but it will, at some point, have been external to the cell into which it is to be introduced.

The term "transgenote" refers to the immediate product of the transformation process and to resultant whole transgenic plants.

DESCRIPTION OF PREFERRED EMBODIMENTS

This invention provides methods and compositions for detecting post-transcriptional gene silencing (PTGS) in a plant cell. The methods involve introducing into the plant cell a nucleic acid that includes a promoter operably linked to a suppression-sensitive reporter (SSR) gene. The SSR gene typically includes a nucleotide sequence that encodes a reporter moiety that can be detected by suitable means, as well as a targeting nucleotide sequence that is substantially identical to the gene of interest. The reporter-encoding nucleotide sequence and the targeting nucleotide sequence are transcribed, under the control of the promoter, as a single mRNA transcript. PTGS is detected as a reduction in the amount of reporter moiety compared to a control plant cell in which the gene of interest is not post-transcriptionally silenced.

The methods and compositions of the invention provide significant advantages over previously available methods for detecting PTGS. For example, unlike screening methods that require an extended period of plant development to produce an appropriate plant tissue for assay, such as flowers or fruit, the screening methods of the invention allow detection of PTGS at an early stage of plant development. An additional advantage is that the screening methods distinguish between low accumulation of a transgene transcript caused by sense suppression and low accumulation that results from other causes such as, for example, insertion of a transgene in a transcriptionally inactive region of the plant genome.

I. Post-Transcriptional Gene Silencing

Post-transcriptional gene silencing (PTGS) can arise as a result of one or more of several mechanisms. For example, PTGS can be the result of antisense suppression, sense suppression, or transgene silencing. Viral resistance is sometimes mediated by PTGS, often as a result of expression in a plant of a transgene derived from a plant virus. "Silencing," as used in the term "post-transcriptional gene silencing," can be full or partial silencing. Thus, PTGS can result in expression of a particular gene being completely suppressed, or can cause only partial suppression.

a. Sense Suppression

Sense suppression refers to a reduction in expression (i.e., repression) of a gene product that can be attained upon introduction into the cell of a nucleic acid that is ultimately transcribed to yield a mRNA transcript that is substantially identical to a portion of the suppressed gene's transcript. The transcript of the introduced transgene is preferably produced prior to production of the transcript of the gene to be suppressed, but may be produced simultaneously with native transcript production. Depending on the time and amount of transcript produced in a transgenote, a plant grown from it may exhibit a variety of different phenotypic traits. The present invention provides screening methods for readily detecting the presence of sense suppression in plant cells. Methods for obtaining sense suppression are described in, for example, U.S. Pat. Nos. 5,034,323, 5,231,020, and 5,283,184. The methods and teachings of these patents are incorporated herein by reference.

The efficiency of production of useful transgenotes that exhibit sense suppression is often variable. The likelihood of obtaining a desirable transgenote will depend upon the number of transgenotes screened and the efficiency of expression of the foreign nucleic acid sequence in transformants. The frequency with which silencing is obtained in a population of plants, each of which is the result of an independent transformation event, can range widely. Often, the frequency is from less than one percent to thirty percent or more. Therefore, the availability of an efficient and effective screening method such as that provided by the invention is a significant improvement over previously available methods.

b. Antisense Suppression

Post-transcriptional gene silencing can also arise as a result of antisense suppression, which involves introducing into a plant cell a nucleotide sequence that, when expressed, produces a transcript which is at least partially complementary to a transcript of a gene of interest. Thus, antisense suppression differs from sense suppression insofar as the polarity of the transcript produced. While sense suppression involves a transcript that is at least substantially identical to a transcript produced by the gene of interest, antisense suppression is effected by production of a transcript that is complementary to the transcript of the gene of interest. Antisense suppression of gene expression in plants is described in, for example, U.S. Pat. Nos. 5,453,566, 5,316, 930, and 5,457,281.

With the exception of the polarity of the transcript produced by the introduced nucleotide sequence, genetic constructs for obtaining antisense suppression are similar to those used for sense suppression. For example, the nucleotide sequence introduced for antisense suppression is typically under the control of a promoter that is function in the plant cell; examples of such promoters are known to those of skill in the art, and several are listed herein. Similar considerations govern the length of introduced nucleotide sequence required and the degree of identity or complementarity required to obtain the desired amount of PTGS. Nucleic acids for introduction into plant cells to obtain PTGS can be identified and obtained as described above.

c. Virus Resistance

Post-transcriptional gene silencing can mediate plant resistance to infection by plant viruses. This phenomenon is described in, for example, U.S. Pat. No. 5,316,930, Mueller et al. (1995) *Plant J* 7: 1001–1013, Goodwin et al. (1996) *Plant Cell* 8: 95–105, English et al. (1996) *Plant Cell* 8: 179–188, and Smith et al. (1994) *Plant Cell* 6: 1441–1453. PTGS-mediated viral resistance can arise by either sense suppression or antisense suppression, or by other mechanisms that result in post-transcriptional gene silencing. Typically, a transgene that is either complementary to (for antisense suppression), or substantially identical to (for sense suppression), a plant virus-derived nucleic acid is introduced into a plant cell. The viral nucleic acid is typically derived from one that is required for one or more viral functions, such as translation of viral proteins, replication of viral RNAs, encapsidation of viral nucleic acid, and the like. Preferably, the transgene is introduced prior to challenge by the virus so that upon actual challenge by the virus, expression of the viral gene that corresponds to the transgene is reduced or eliminated by post-transcriptional gene silencing.

II. Screening for Post-Transcriptional Gene Silencing using Suppression-Sensitive Reporter Genes The invention provides, in one embodiment, methods for detecting post-transcriptional gene silencing in a plant cell. The methods involve introducing into the plant cell a suppression-sensitive reporter (SSR) gene, which includes a nucleotide sequence that encodes a reporter moiety and also includes a targeting nucleotide sequence. The reporter-encoding nucleotide sequence and the targeting sequence are normally transcribed as a single mRNA transcript. The screening methods provided by the invention permit one to screen large numbers of cells, protoplasts, or other transformed tissue without the necessity of completely regenerating intact plants from the tissues.

The targeting nucleotide sequence present in an SSR gene is at least substantially identical to all or part of a transcript that is produced by a gene of interest. The chosen gene can be an endogenous plant gene, a transgene, or a gene that may be introduced into the plant cell by, for example, a plant virus. The degree of sequence identity between the gene's transcript and the targeting sequence is typically at least about 65%, more preferably at least about 80%, and most preferably about 95% to absolute identity. Where the method is used to detect transgene-induced sense suppression, the targeting sequence is, by virtue of its similarity to the chosen gene's transcript, generally substantially identical to all or a subsequence of the transcript produced by the transgene as well. For detection of antisense-mediated PTGS, the targeting sequence is complementary to the antisense nucleic acid. The targeting sequence of the SSR gene can be longer, shorter, or the same length as the transgene or endogenous gene. Generally the targeting sequence is preferably at least about 100 bp in length, although shorter sequences are also functional.

An SSR gene also includes a reporter nucleotide sequence, which encodes a reporter moiety. The presence or absence of the reporter moiety is readily detectable through use of an appropriate assay that, in a preferred embodiment, does not require extensive development of transgenic plants or complex biochemical or other assays. Suitable reporter moieties are known to those of skill in the art. Such preferred reporters include, but are not limited to, β-glucuronidase (GUS, uidA) from *E. coli*, luciferase (LUC) from firefly, and green fluorescent protein (GFP) from jellyfish. Each of these systems are well-characterized. The nucleotide sequence of the GUS gene and its use to construct chimeric reporter genes is described in, for example, Jefferson et al. (1987) *Plant Mol. Biol. Reporter* 5: 387) and Jefferson et al. (1986) *Proc. Nat'l. Acad. Sci.* USA 83: 8447. Detection of GUS expression is possible using a wide variety of β-glucuronides, including many substrates that are chromogenic and/or fluorogenic. Thus, one can use histochemical, spectrophotometric, and fluorometric means for detecting GUS gene expression; quantitation of the level of GUS expression is thus possible. Systems for detection of the GUS gene product are commercially available (see, e.g., ImaGene Green C 12 FDGlcU GUS Gene Expression Kit, Molecular Probes, Eugene Oreg.). One preferred embodiment is a GUS-int chimeric gene that has cloning sites just past the stop codon of the GUS coding sequence for insertion of a targeted sequence. Vancanneyt et al. (1990) *Mol. Gen. Genet.* 220: 245–250. Another preferred reporter moiety is the gene encoding green fluorescent protein (GFP), which gene product is intrinsically fluorescent. Chalfie et al. (1994) *Science* 263: 802. Luciferase is another readily detectable enzyme that is suitable for use as a reporter. DeWet et al. (1987) *Mol. Cell. Biol.* 7: 725. Other suitable reporters, including chloramphenicol acetyltransferase (CAT), are known to those of skill in the art.

Where the SSR gene is introduced into a plant cell by Agrobacterium or other bacteria-mediated gene transfer, it is desirable that the reporter moiety not be expressed in the bacterial cells. This can be achieved by, for example, the insertion of an intron into the SSR gene such that the intron prevents expression in bacterial cells but the transcript is properly spliced in plant cells to create an mRNA that is capable of functional expression. Alternatively, one can insert a bacterial transcription termination signal into the plant promoter or leader sequence.

In a typical embodiment, the reporter-encoding nucleotide sequence and the targeting nucleotide sequence are transcribed in a plant cell as a single transcription unit. For example, one can insert the targeting sequence into the reporter nucleotide sequence at any location that is consistent with retention of reporter gene function. Preferred locations include untranslated regions of the reporter nucleotide sequence, including both the 5' and 3' untranslated regions. Alternatively, one can insert the targeting nucleotide sequence, in the proper reading frame, within the coding region of the reporter nucleotide sequence itself. Conveniently, one or more restriction sites can be placed at a suitable location in the reporter nucleotide sequence to facilitate cloning of various targeting nucleotide sequences into the SSR gene. A schematic diagram of a SSR gene is shown in FIG. 1.

The SSR gene is placed under the control of a promoter that drives expression of the gene. A promoter can be derived from gene that is under investigation, or can be a heterologous promoter that is obtained from a different plant gene, or from a different plant species. Where direct expression of the SSR gene in all tissues of a transgenic plant is desired, one can use a "constitutive" promoter, which are generally active under most environmental conditions and states of development or cell differentiation. Examples of constitutive promoters of plants include the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Such promoters include those obtained from Ti- or Ri-plasmids, from plant cells, plant viruses or other hosts where the promoters are found to be functional in plants. Bacterial promoters that function in plants, and thus are suitable for use in SSR genes include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the ,β-conglycinin promoter, the phaseolin promoter, the ADH promoter, and heat-shock promoters.

Alternatively, the SSR gene can be placed under the control of a promoter that directs expression of SSR gene in a specific tissue (tissue-specific promoters) and/or under more precise environmental control (inducible promoters). Examples of tissue-specific plant promoters under developmental control include promoters that initiate transcription only in certain tissues, such as fruit, seeds, or flowers. The tissue specific E8 promoter from tomato is particularly useful for directing gene expression so that a desired gene product is located in fruits. See, e.g., Lincoln et al. (1988) *Proc. Nat'l. Acad. Sci.* USA 84: 2793–2797; Deikman et al. (1988) *EMBO J.* 7: 3315–3320; Deikman et al. (1992) *Plant Physiol.* 100: 2013–2017. Other suitable promoters include those from genes encoding embryonic storage proteins. Examples of environmental conditions that may affect transcription by inducible promoters include anaerobic conditions, elevated temperature, or the presence of light.

The SSR gene construct can also include a polyadenylation region at the 3'end of the coding region. The polyadenylation region can be derived from the natural gene, from a variety of other plant genes, or from T-DNA. Polyadenylation sites are commonly recognized by the presence of homology to the canonical form 5'. . . AATAAA . . . 3', although variations are not uncommon. See, e.g., McDevitt et al. (1984) *Cell* 37: 993–999; Proudfoot, N. (1984) *Nature* 307:412–413; Birnstiel et al. (1985) *Cell* 41:349–359.

To facilitate the insertion of the SSR gene into plant cells, the gene is typically placed in a vector. Selection of an appropriate vector is relatively simple, as the constraints are minimal. The apparent minimal traits of the vector are that the desired nucleic acid sequence be introduced in a relatively intact state. Thus, any vector which will produce a plant carrying the introduced SSR gene should be sufficient. Also, any vector which will introduce a substantially intact RNA which can ultimately be converted into a stably maintained DNA sequence is also acceptable. Even a naked piece of DNA would be expected to be able to confer the properties of this invention, though at lower efficiency. The decision as to whether to use a vector, or which vector to use, will be guided by the method of transformation selected.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including RNA forms of the SSR gene sequences. The selection of vectors and methods to construct them are commonly known to persons of ordinary skill in the art and are described in general technical references (see, e.g., *Methods in Enzymology*, Vol. 153 ("Recombinant DNA Part D") 1987, Wu and Grossman Eds., Academic Press). Any additional attached vector sequences which will confer resistance to degradation of the nucleic acid fragment to be introduced or which assists in the process of genomic integration are advantageous.

Cauliflower mosaic virus (CaMV) can also be used as a vector for introducing the foreign nucleic acid into plant cells (Hohn et al. (1982) *Molecular Biology of Plant Tumors*, Academic Press, New York, pp. 549–560; Howell, U.S. Pat. No. 4,407,956). CaMV viral DNA genome is inserted into a parent bacterial plasmid creating a recombinant DNA molecule which can be propagated in bacteria. After cloning, the recombinant plasmid again can be cloned and further modified by introduction of the desired DNA sequence into the unique restriction site of the linker. The modified viral portion of the recombinant plasmid is then excised from the parent bacterial plasmid, and used to inoculate the plant cells or plants.

A preferred vector for introducing an SSR gene into many types of plant cell is the Ti plasmid of *Agrobacterium tumefaciens*. The Ti plasmid is transmitted to plant cells upon infection by *A. tumefaciens*, and is stably integrated into the plant genome (Horsch et al. (1984) *Science* 233: 496–498; Fraley et al. (1983) *Proc. Nat'l. Acad. Sci. USA* 80: 4803). Ti plasmids contain two regions essential for the production of transformed cells. One of these, named transfer DNA (T DNA), induces tumor formation when the T DNA is in its native state. The other, referred to as the virulent region, is essential for the introduction of the T DNA into plants. The transfer DNA region, which becomes integrated into the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector." Often, much of the DNA found between the two T DNA borders in a native Ti plasmid is deleted and the SSR and/or additional genes is placed between the borders. Upon infection and transformation of the plant cells, this DNA that is flanked by the T DNA borders becomes integrated into the plant cell genome.

To detect the presence of post-transcriptional gene silencing, the SSR gene is introduced into a plant cell by methods known to those of skill in the art. The presence or absence of the reporter moiety is then detected after sufficient time to allow for expression of the reporter moiety. Methods and reagents for detecting particular reporter moieties are well known in the art. See, e.g., Jefferson et al. (1987) *EMBO J.* 6: 3901–3907; Ow et al. (1986) *Science* 234: 856–859. General descriptions of plant expression vectors and reporter genes, and methods for their use, are found in Gruber et al., "Vectors for Plant Transformation," in *Methods in Plant Molecular Biology and Biotechnology*, Glick et al. (eds.), pages 89–119 (CRC Press, 1993). GUS expression vectors and GUS gene cassettes are commercially available from Clontech Laboratories, Inc. (Palo Alto, Calif.), while luciferase expression vectors and luciferase gene cassettes are available from Promega Corporation (Madison, Wis.).

Suitable plant tissues for this method include, but are not limited to, a leaf explant, flower, root, stem, and callus. Methods of preparing a plant or plant tissue for detection of a reporter moiety are known to those of skill in the art. For example, one can homogenize the tissue and assay for reporter expression in vitro. Conveniently, the plant cells are placed on a medium that contains a substrate for the particular reporter moiety. Those transgenic plants or tissues that produce reduced amounts of the reporter moiety compared to control plants (for example, plant tissues that do not contain the SSR gene) are identified as exhibiting post-transcriptional gene silencing. Reporter-substrate combinations that provide visually detectable results are preferable.

Typically, the PTGS that is detected using the methods of the invention is induced by a transgene, as described above. A separate transgene that produces a transcript that is substantially identical to the gene to be repressed is introduced into the plant cell. Where the methods are used to identify plants that are candidates for being resistant to infection by a plant virus, the transgene is typically substantially identical to, or substantially complementary to, all or a portion of a viral gene. An SSR gene that includes a targeting nucleotide sequence that is at least substantially identical to the viral gene is introduced into plant cells containing the viral transgene, and the cells are assayed for the level of expression of the reporter moiety. Those plants or plant tissues that exhibit a reduced level of SSR gene expression, and thus post-transcriptionally silence expression of the virus-derived transgene, are generally able to suppress expression of the corresponding gene when introduced into the plant cell by means of an infecting virus.

Another embodiment of the invention involves the use of a non-suppressible reporter (NSR) gene in conjunction with an SSR gene. The NSR gene, which includes a reporter gene but, unlike the SSR gene, does not include a targeting nucleotide sequence. The SSR and NSR genes encode different reporter activities so that one can determine the expression levels of each gene independently. Preferably, the NSR gene is expressed under the same conditions as is the SSR gene when both are introduced into a plant cell. The presence of an NSR gene as well as the SSR gene permits one to normalize for variable levels of DNA delivery by quantitating NSR and SSR gene expression levels and determining the ratio. The extent of post-transcriptional gene silencing is calculated as the ratio of SSR activity/NSR activity in a test plant as compared to the SSR activity/NSR activity ratio in a control plant. Thus, quantitative assessment of the degree of PTGS is facilitated.

The NSR and SSR genes can be introduced into a plant cell simultaneously or at different times. Separate vectors can be used for each reporter gene, or the two genes can be introduced into a plant cell in a single vector. In a preferred embodiment, the NSR and SSR genes are both present between the same pair of functional T DNA borders for introduction into plant cells by Agrobacterium. Alternatively, the two reporter genes are introduced between two different pairs of T DNA borders, which may or may not be present on the same vector. If both genes are present within a single set of T DNA borders, they can be introduced by cocultivation with a single Agrobacterium strain. If the two genes are present between separate T DNA borders, the genes can be introduced into the same Agrobacterium cells or into different bacterial strains that are cultured and then cocultivated together with the plant cells.

Also provided by the invention are methods for assaying a plant to determine whether a selected gene is post-transcriptionally suppressed. The method involves introducing into plant cells a nucleic acid that includes a promoter operably linked to a suppression-sensitive reporter gene. The SSR gene includes a targeting nucleotide sequence that produces a transcript that is substantially identical to a transcript produced by the selected gene, and also includes a reporter gene that is transcribed as a single transcript with the targeting nucleotide sequence. Once cells containing the SSR gene are obtained, the level of expression of the reporter gene is determined, either quantitatively or qualitatively, to ascertain whether post-transcriptional gene silencing of the selected gene has occurred. The assay methods can also include the introduction of a NSR gene to allow normalization of the assay results.

III. Target Plants and Phenotypic Modifications

Post-transcriptional gene silencing (PTGS), and methods for detecting such suppression, are useful in regulating expression of many plant genes. The methods of the invention are useful for detecting PTGS that can result in modification of various phenotypic traits that include, but are not limited to, visible traits, environmental or stress related traits, disease related traits, and ripening traits. The repressive effect of PTGS is applicable to a variety of genes expressed in plants including, for example, genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, storage proteins, phenolic acids, coumarins, alkaloids, quinones, lignins, glucosinolates, tannins, aliphatic amines, celluloses, polysaccharides, glycoproteins and glycolipids.

For instance, the screening methods provide a convenient, rapid, and sensitive method for identifying plants in which PTGS results in an alteration in the production of fatty acids or lipids (and fatty acid composition of, e.g., an oil-producing plant thus altered) by blocking synthesis of a specific chain elongation or desaturation enzyme. The oils are lipids which typically are liquid at room temperatures and typically will have various unsaturations in the fatty acid components and shorter lipid chains than the fats. See generally, Lehninger (1978) *Biochemistry*(2d Ed), Worth Publishers, New York; and Bonner and Varner (1976) *Plant Biochemistry*(3d Ed), Academic Press, New York. Much is also known about the applicable biosynthetic pathways at the genetic level. See, e.g., the following, and references cited therein: Shure et al. (1984) *Cell* 35: 225–233; Preiss et al., *Tailoring Genes for Crop Improvement* (Bruening et al., eds.), Plenum Press (1987) pp. 133–152; Gupta et al. (1988) *Plant Mol. Biol.* 10: 215–224; Olive et al. (1989) *Plant Mol. Biol.* 12: 525–538; and Bhattacharyya et al. (1990) *Cell* 60:155–122.

For example, such PTGS can be induced by introducing into a plant cell a nucleotide sequence that encodes an enzyme involved in lipid metabolism, with the suppression modifying the metabolism of oils and other lipids, such as fats. The relative proportions or absolute content of various different types of oils may be thereby altered, and using information known in the art about sugar-starch biosynthetic pathways at the genetic level (see, e.g., citations on same above). Various enzymes of particular interest include, among others, stearyl desaturase, acetyl transacylase, malonyl transacylase, β-ketoacyl ACP-synthetase, β-keto ACP-reductase, enoyl ACP-hydrase, acyl-ACP thioesterases and enoyl ACP-reductase. The methods provided by the invention allow one to identify plants having PTGS-induced alterations in oil and lipid metabolism without having to undertake biochemical analysis of resulting plants. A SSR gene is used that includes as a targeting equence a portion of the oil or lipid metabolism gene for which suppression is desired. Plant tissue in which the reporter moiety is expressed at a significantly lower level than in control plants are likely to exhibit sense suppression of the desired gene.

The screening methods described herein are also useful for identifying plants in which PTGS has resulted in an increase or decrease in the synthesis of starch and/or other carbohydrates, thus modifying the sugar content of, e.g., an edible plant thus altered) by blocking an enzyme required for starch synthesis. For example, genes encoding enzymes used in carbohydrate metabolism, e.g, in the metabolism of amylose, pectins, cellulose and cell walls, are used to suppress enzymatic expression and activity to modify sizes of pools of metabolic intermediates or kinetics of conversion, thereby changing the starch or sugar contents of various plants. Various enzymes of particular interest in carbohydrate metabolism include phosphorylase, starch synthetase, Q-enzyme, sucrose-6-phosphate synthetase, sucrose-6-phosphate phosphatase, ADP-glucose pyrophosphorylase and various amylases. See generally, Bonner and Varner (Eds) (1976) *Plant Biochemistry*(3d ed.), Academic Press, New York. Much is also known about the applicable biosynthetic pathways at the genetic level. See, e.g., the following, and references cited therein: Stefansson et al. (1961) *Can. J Plant Sci.* 41: 218–219; Knowles et al. (1972) *Oil Crops of the World (Robbelen et al., eds.), McGraw-Hill,* pp. 260–282; Hammond et al. (1983) *Crop Sci.* 23: 192–197; Widstrom et al. (1984) *Crop Sci.* 24: 1113–1115; Green et al. (1984) *Euphytica* 33:321–328; Graefet al. (1985) *Crop Sci.* 25:1076–1079; Somerville et al., *Recent Advances in Phytochemistry* (Conn, ed.), Plenum Press (1988), pp. 19–44; Kunst et al. (1988) *Proc. Nat'l. Acad. Sci. USA* 85: 4143–4147; and Browse et al., "Strategies for Modifying Plant Lipid Composition" (1989) In *Plant Gene Transfer* (Lamb, C. et al., eds.), Alan R. Liss.

To identify such plants without having to undertake biochemical analysis or wait for the plants to reach maturity, all or part of the nucleic acid used to effect sense suppression is used as the targeting moiety for an SSR gene. Transgenic plant tissues are then examined to detect the presence or absence of the reporter moiety encoded by the SSR gene. A decrease in the level of reporter moiety is indicative of PTGS. Similarly, the screening methods are useful for identifying plants in which PTGS is effective for altering the release of fragrant molecules from cells (thus altering the scent characteristics of, e.g., ornamental flowers) by blocking expression of the enzymes responsible for glycosylation of such molecules.

As another example, one can use the screening methods of the invention to identify plants in which PTGS modifies plants that express the flavonoid pathway genes, which are involved providing color to various plant tissues. At least some of the flavonoid pathway genes are essentially ubiquitous in higher plants; their products are found in flowers or other plant organs (such as leaves, stems, roots, tubers, bracts, sepals, fruits, vegetables) which are colored. These colors are provided largely by anthocyanin pigments, other flavonoid pigments, copigments, or colorless flavonoids synthesized from chalcone by the plant. See, e.g, Hahlbrock (1981) *Biochemistry of Plants*, Vol. 7, Conn (Ed.); Harborne, (1986) *Plant Flavenoids in Biology and Medicine: Biochemical Pharmacological and Structure Activity Relationships;* Harborne, (1976) *Chemistry and Biochemistry of Plant Pigments*, (2d ed.) Vol. 1, Goodwin (Ed.) Acad. Press. Anthocyanin pigmented flowers have colors throughout the range orange to red to purple to blue. Chalcones and aurones are yellow or orange. Flavones and flavonols are very light yellow, or "cream" colored. Flavanones are colorless. Elimination of anthocyanins and diversion of the pathway to flavone or flavonol production would create cream colored flowers. Shifts from blue to purple or purple to red or red to orange can be engineered by interfering with 3' or 5' hydroxylases of 2-hydroxylases. Interference with 2-hydroxylases can also reduce color intensity of anthocyanin pigmented plants. Interference with CHS would create white flowers and with chalcone isomerase would create yellow flowers. A wide variety of bi-color patterns can be created, the two colors being the color of the target plant before engineering and the color resulting from the expression of the introduced flavonoid gene. Types of patterns include: radial star-like patterns; picotee (white outer edge); white annular center; concentric colored rings; erratic, irregular patterns, e.g., variegated or blotchy. There are many variations on these patterns, some more attractive than others, some with sharp boundaries between colors, some with diffuse boundaries, some with linear boundaries, some with wavy, curved boundaries. Also lighter, solid colors are observed.

The class of genes within the flavonoid biosynthetic pathway which can be used for PTGS, and also as targeting moieties for a SSR gene, includes those nucleic acid sequences directly involved in reactions or control of reactions which synthesize or modify a flavonoid compound. Flavonoids are a class of compounds, numbering about 3000 whose functions in plants include coloration in flowers, fruits, leaves, and other organs. Examples of flavonoid biosynthetic genes include those for chalcone synthases, chalcone isomerases (CHI), flavanone 3-hydroxylases, dihydroflavonol reductases, flavanone 2-hydroxylases, dihydroflavanol 2-hydroxylases, flavonoid 3'-hydroxylases, flavonoid 5'-hydroxylases, flavonoid glycosyltransferases (including glucosyl transferases such as UDPG: flavonoid 3-O-glucosyl transferase and UDPG: flavonol 7-O-glucosyl transferase, and rhamnosyl transferases), flavonoid methyltransferases (such as SAM:anthocyanidin 3-(p-coumaroyl)-rutinoside-5-glucoside 3',5'-O-methyltransferase) and flavonoid acyltransferases. See, Hahlbrock (1981) *Biochemistry of Plants*, Vol. 7, Conn (Ed.); Weiring and de Vlaming (1984) "Petunia", K. C. Sink (Ed.), Springer-Verlag, New York. By way of example of the components of these pathways, phenylalanine is converted to cinnamic acid; cinnamic acid is converted to caffeic acid (in a side branch) and to coumaryl-coenzyme A; coumaryl-coenzyme A is converted with chalcone synthase to a tetrahydroxy chalcone; the tetrahydroxy chalcone is converted with chalcone isomerase to naringenin; and naringenin is converted in a subsequent series of steps to anthocyanins. Blockage or inactivation at a given stage leads to build-up of precursors and side chain products of precursors. For instance, blockade at the chalcone synthase stage leads to build-up of coumaric acid and caffeic acid.

Post-transcriptional gene silencing is useful for modifying the color of plant tissues such as fruit (e.g., apples, cherries, plums, grapes), vegetable (e.g., eggplant, peppers, kale, lettuce, radishes, cauliflower) or other edible plant parts (e.g., potato). Flower colors, of course, are commonly very dependent on the activity of the flavonoid pathway genes, and thus are especially sensitive to the absolute and relative levels of expression of the flavonoid biosynthetic pathway genes. Ornamental plants and flowers are valuable commercially, and thus are typical targets of sense suppression methods. Creation and selection of new coloration schemes are particularly valuable in the ornamental flower bearing plants such as chrysanthemums, carnations, roses, gerberas, lilies, geraniums, poinsettias and petunias.

The screening methods described herein provide an efficient and convenient means by which to identify plants that exhibit post-transcriptional silencing of genes involved in flavonoid biosynthesis. Unlike previously available screening methods, one need not wait until plants have reached a late stage of maturity such that flowers and/or fruit have developed. Instead, one can screen plants at a much earlier stage of development when using the SSR gene screening methods of the invention.

Also provided by the invention are methods for identifying plant cells that are resistant to infection by plant viruses by virtue of PTGS. Plant viruses against which one can obtain resistance by PTGS include, but are not limited to, those of the following genera: Alfamoviruses: Bromoviridae, Alphacryptoviruses: Partitiviridae, Badnaviruses, Betacryptoviruses: Partitiviridae, Bigeminiviruses: Geminiviridae, Bromoviruses: Bromoviridae, Bymoviruses: Potyviridae, Capilloviruses, Carlaviruses, Carmoviruses: Tombusviridae, Caulimoviruses, Closteroviruses, Comoviruses: Comoviridae, Cucumoviruses: Bromoviridae, Cytorhabdoviruses: Rhabdoviridae, Dianthoviruses, Enamoviruses, Fabaviruses: Comoviridae, Fijiviruses: Reoviridae, Furoviruses, Hordeiviruses, Hybrigeminiviruses: Geminiviridae, Idaeoviruses, Ilarviruses: Bromoviridae, Ipomoviruses: Potyviridae, Luteoviruses, Machlomoviruses, Macluraviruses, Marafiviruses, Monogeminiviruses: Geminiviridae, Nanaviruses, Necroviruses, Nepoviruses: Comoviridae, Nucleorhabdoviruses: Rhabdoviridae, Oryzaviruses: Reoviridae, Ourmiaviruses, Phytoreoviruses: Reoviridae, Potexviruses, Potyviruses: Potyviridae, Rymoviruses: Potyviridae, Satellite RNAs, Satelliviruses, Sequiviruses: Sequiviridae, Sobemoviruses, Tenuiviruses, Tobamoviruses, Tobraviruses, Tombusviruses: Tombusviridae, Tospoviruses: Bunyaviridae, Trichoviruses, Tymoviruses, Umbraviruses, Unassigned potyviruses: Potyviridae, Unassigned rhabdoviruses: Rhabdoviridae, Varicosaviruses, and Waikaviruses: Sequiviridae, as well as ungrouped plant viruses. Brunt et al. (eds.) (1996 onwards). 'Plant Viruses Online: Descriptions and Lists from the VIDE Database. Version: Jan. 16, 1997.' URL, Dallwitz, M. J. (1980) *Taxon* 29: 41–46; Dallwitz et al. (1993) User's Guide to the DELTA System: a general system for processing taxonomic descriptions. 4th edition. 136 pp. (CSIRO Division of Entomology: Canberra). For example, the methods of the invention are useful for identifying PTGS-mediated resistance to potato virus Y and related potyviruses, tobacco etch virus, tobacco vein mottling virus, and other commercially significant plant pathogens.

IV. Transformation and Regeneration

The introduction of SSR and NSR genes into plants in accordance with the methods of the invention may be carried out in essentially any of the various ways known to those skilled in the art of plant molecular biology. See, in general, *Methods in Enzymology* Vol. 153 ("Recombinant DNA Part D") 1987, Wu and Grossman Eds., Academic Press. One method by which one can introduce a foreign nucleic acid into plant cells is by transfer of the foreign nucleic acid into the plant cell by using polyethylene glycol, which forms a precipitation complex with the genetic material that is taken up by the cell (Paszkowski et al. (1984) *EMBO J.* 3:2717–22). Alternatively, an introduced gene may be introduced into the plant cells by electroporation (Fromm et al. (1985) *Proc. Nat'l. Acad. Sci. USA* 82: 5824). In this technique, plant protoplasts are electroporated in the presence of plasmids or other nucleic acids containing the relevant genetic construct. Electrical impulses of high field strength reversibly permeabilize biomembranes, allowing the introduction of the nucleic acids. Electroporated plant protoplasts reform the cell wall, divide, and form a plant callus. Selection of the transformed plant cells with the transformed gene can be accomplished using phenotypic markers.

Another method of introduction of nucleic acid segments into plant cells is high velocity ballistic penetration by small particles with the nucleic acid either within the matrix of small beads or particles, or on the surface (Klein et al. (1987) *Nature* 327: 70–73; McCabe et al. (1988) *Biotechnology* 6: 923–936). Although typically only a single introduction of a new nucleic acid segment is required, this method particularly provides for multiple introductions.

A preferred method of introducing the nucleic acid segments into plant cells is to infect a plant cell, an explant, a meristem or a seed with *Agrobacterium tumefaciens* that is transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. A binary system is often used, in which one plasmid contains the T-DNA and a second plasmid contains the vir region. Infection requires the presence of both plasmids in an Agrobacterium cell. Any one of a No. of T-DNA containing plasmids can be used, the only requirement is that one be able to select independently for each of the two plasmids. After transformation of the plant cell or plant, those plant cells or plants transformed by the Ti plasmid so that the desired DNA segment is integrated can be selected by an by an appropriate phenotypic marker. These phenotypic markers include, but are not limited to, antibiotic resistance, herbicide resistance or visual observation. Other phenotypic markers are known in the art and may be used in this invention.

There are presently several different ways to transform plant cells with Agrobacterium. First, one can co-cultivate Agrobacterium with cultured isolated protoplasts. This requires an established culture system that allows culturing of protoplasts and regeneration of plants from the cultured protoplasts. Plants for which co-cultivation of Agrobacterium with protoplasts provides a feasible method for generation of transgenic plants include, for example, species from the genera Fragaria, Lotus, Medicago, Onobrychis, Trifolium, Trigonella, Vigna. Citrus, Linum, Geranium, Manihot, Daucus, Arabidopsis, Brassica, Raphanus, Sinapis, Atropa, Capsicum, Hyoseyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus. Senecio, Salpiglossis, Cucumis, Browaalia, Glycine, Lolium, Zea, Triticum, Sorghum, and Datura.

A second method of using Agrobacterium to obtain transgenic plants is to transform plant cells or tissues with Agrobacterium. Typically, it is desirable to use cells or tissues from which one can induce regeneration into intact plants after transformation. A third method involves transforming seeds, apices, or meristems with Agrobacterium. These tissues can then be micropropagated to obtain intact plants. It is known that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Although monocotyledonous plants, and in particular, cereals and grasses, are not natural hosts to Agrobacterium, work to transform them using Agrobacterium has also been carried out (Hooykas-Van Slogteren et al. (1984) *Nature* 311:763–764). Additional plant genera that can be transformed by Agrobacterium include Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus and Pisum.

Once the methods of the invention have been used to identify plant cells that exhibit PTGS, or that lack PTGS, as desired, the cells can be regenerated to obtain a whole plant from the transformation process. Plant regeneration from cultural protoplasts is described in Evans et al., "Protoplasts Isolation and Culture," *Handbook of Plant Cell Cultures* 1: 124–176 (MacMillan Publishing Co. New York 1983); M. R. Davey, "Recent Developments in the Culture and Regeneration of Plant Protoplasts," *Protoplasts* (1983) Lecture Proceedings, pp.12–29, (Birkhauser, Basal 1983); P. J. Dale, "Protoplast Culture and Plant Regeneration of Cereals and Other Recalcitrant Crops," *Protoplasts* (1983) Lecture Proceedings, pp. 31–41, (Birkhauser, Basel 1983); and H. Binding, "Regeneration of Plants," *Plant Protoplasts*, pp.21–73, (CRC Press, Boca Raton 1985).

Regeneration from protoplasts varies from species to species of plants, but generally a suspension of transformed protoplasts containing copies of the exogenous sequence is first made. In certain species embryo formation can then be induced from the protoplast suspension, to the stage of ripening and germination as natural embryos. The culture media will generally contain various amino acids and hormones, such as auxin and cytokinins. It is sometimes advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Regeneration also occurs from plant callus, explants, organs or parts. Transformation can be performed in the context of organ or plant part regeneration. *Methods in Enzymology*, Vol. 153, supra.; also *Methods in Enzymology*, Vol. 118; and Klee et al. (1987) *Annual Review of Plant Physiology* 38: 467–486. For vegetatively propagated crops, the mature transgenic plants are propagated by the taking of cuttings or by tissue culture techniques to produce multiple identical plants. After identification of plants that exhibit the desired sense suppression of a particular gene, the plants are propagated vegetatively for commercial sale.

For seed propagated crops, the mature transgenic plants may be self crossed to produce a homozygous inbred plant. The inbred plant produces seed containing the gene for the newly introduced foreign gene activity level. These seeds can be grown to produce plants that would produce the selected phenotype.

The inbreds obtained using the screening methods of the invention can be used to develop new hybrids. In this method a selected inbred line is crossed with another inbred line to produce the hybrid.

The invention also provides plants, and parts obtained from such plants, that are identified using a suppression-sensitive reporter gene as described herein. Plant parts within the scope of the invention include flowers, seeds, leaves, branches, fruit, and the like. Progeny and variants, and mutants of the regenerated plants are also included within the scope of this invention, as well as later descendants of plants obtained through use of the screening methods.

EXAMPLES

The following examples are offered to illustrate, but not to limit the present invention.

Example 1
Construction of a Suppression Sensitive Reporter

This Example describes the construction of a suppression sensitive reporter using the bacterial β-glucuronidase coding sequence (uidA gene or GUS) and a targeting sequence which renders the reporter sensitive to the suppressed state of the tomato LE-ACS-2 gene. All manipulations were performed using standard techniques as described in Sambrook et. al. ((1989) *Molecular Cloning-A Laboratory Manual* (2nd ed.) Vol. 1–3, Cold Spring Harbor Laboratory, Cold Spring Harbor Press, N.Y.).

A multiple cloning region was introduced into the unique XbaI site of pJJ3431 (a pUC-118 derivative containing a CaMV 35S promoter driving GUS coding sequences followed by the octopine synthase polyadenylation sequences) by linearizing with XbaI and ligating an adapter formed by annealing two oligonucleotides: NC-201 (5'-CTAGTAGGATCCGGTACCATCGATTCTAGAC-3', SEQ ID NO:1) and NC-202 (5'-CTAGGTCTAGAATCGATGGTACCGGATCCTA-3', SEQ ID NO:2). The ligated molecules were transformed into *E. coli* DH5α and growth selected on medium containing ampicillin. Plasmids were screened by minipreps and those with the correct restriction pattern were sequenced to verify the structure of the multiple cloning region. Two different plasmids were identified, pPO7066 was determined to have the multiple cloning region in the orientation BamHI-KpnI-ClaI-XbaI followed by the octopine synthase polyadenylation sequences, and pPO7067 had the multiple cloning region in the reverse orientation such that the order of the restriction sites was XbaI-ClaI-KpnI-BamHI followed by the octopine synthase polyadenylation sequences.

The GUS coding region, which is interrupted by an intron, was removed from pLVC-345 (which contains the GUSint gene described by Vancanneyt et al. (1990) *Mol. Gen. Genet.* 220: 245–250) by partial digestion with EcoRV followed by complete digestion with NcoI. The 2.0 kb NcoI-EcoRV fragment was gel purified by adsorption to powdered glass and ligated to either pPO7066 or pPO7067 which had previously been digested with BamHI (pPO7066) or XbaI (pPO7067), blunt-ended with T4 DNA polymerase, and then digested to completion with NcoI. The ligated molecules are used to transform *E.coli* DH5α to ampicillin resistance. The resulting plasmids contain the CaMV 35S promoter, followed by the intron-containing GUS gene (GUSint), the multiple cloning region (KpnI-ClaI-XbaI for pPO7086 and XbaI-ClaI-KpnI-BamHI for pPO7090) and the octopine synthase polyadenylation sequence. Either plasmid can be used for the construction of the LE-ACS-2 suppression sensitive GUS gene; pPO7090 was used in the following experiment.

An LE-ACS-2 cDNA fragment was amplified from pSpMas/GUS/ACCS2 using oligonucleotide primers NC-190 (5'-CGGCCATGGGTTTAGCAGAAAATCAGC-3', SEQ ID NO:3) and NC-191 (5'-CGGCCATGGAACAAACTCGAAACCAACCTGG-3', SEQ ID NO:4) by the polymerase chain reaction using 1 μM each primer, 1.5 mM MgCl$_2$, 50 mM KCl, 10 mM Tris-HCl pH9.0 (at 25° C.), 0.1% Triton X-100 and 0.2 mM for each of dNTPs. The cycling conditions consisted of 35 cycles with 30 seconds at 95° C., 30 seconds at 55° C., and 2 minutes at 72° C. These primers anneal at positions 250–262 (NC-190) and 1312–1333 (NC-191) of the ptACC2 cDNA (GenBank accession number X59145) and produce a 1.1 kb product. The 1.1 kb product was subcloned into the EcoRV site of pBluescript SK(+) (Stratagene, La Jolla Calif.) giving rise to pPO7084. The LE-ACS-2 fragment was retrieved from pPO7084 by digestion with NcoI, the ends were made blunt with Pfu polymerase, and the fragment was gel purified by adsorption to glass powder and cloned into pPO7090 which was previously digested with BamHI, dephosphorylated with alkaline phosphatase and filled in with Pfu polymerase. A plasmid was identified (pPO7099) which contains the LE-ACS-2 fragment inserted in the 3' untranslated region of the GUSint gene in the sense orientation with respect to the GUS coding region.

The entire CaMV 35S -GUSint-LE-ACS-2-OCS gene was excised from pPO7099 via digestion with PvuII, and the 5.19 kb fragment purified by adsorption to powdered glass. The fragment was ligated to pNG5185, a T-DNA-containing plasmid capable of replication in *Agrobacterium tumefaciens*, that was previously digested with SmaI. The ligated molecules were used to transform *E. coli* DH5α to tetracycline resistance and screened by minipreps. A suitable plasmid, pPO7110, was identified which contains the suppression sensitive GUS gene between the T-DNA borders. This plasmid was transformed into the Agrobacterium strain LBA4404 and the resulting strain used to transform tomato leaves.

Example 2
Visual Assay of the Suppression Sensitive Reporter

For tomato transformations, young, fully expanded leaves were collected from 6 week old tomato plants of lines 91103 (nontransformed control) and 1345 (an LE-ACS-2 suppressant) and surfaced sterilized in 70% ethanol. Two 4 mm discs were cut from each leaf and placed into a solution of Agrobacteria harboring either the suppression-sensitive GUS reporter construct pPO7110 or a control, nonsuppression-sensitive GUS construct, such as pPO7113, that lacks LE-ACS-2 sequences but is identical in every other respect. The Agrobacteria were previously grown in minimal medium containing sucrose and tetracycline at 1 mg/l to an apparent optical density of about 0.2 at 550 nm. Cultures at densities ranging from 0.1–0.4 were used, but the final density was always adjusted to 0.2 at 550 nm using growth medium. Discs were incubated with the Agrobacteria for 0.5–1.5 minutes, then removed and placed on sterile filter paper that was placed on top of tomato cocultivation medium (MS salts with IAA @ 0.05 mg/l, zeatin @ 1 mg/l and 100 μM acetosyringone and 1% gelrite).

The plates were incubated at 28° C. in the dark for 2.5 days whereupon the discs were removed and stained for GUS activity using 5-bromo-4-chloro-3-indolyl β-D-glucopyranoside (X-Gluc). The discs were vacuum infiltrated for 2 minutes with the substrate solution containing 100 mM potassium phosphate pH 7.0, 10 mM EDTA, 2 mM potassium ferricyanide, 2 mM potassium ferrocyanide, 500 mg/l X-Gluc, and 0.1% Triton X-100. Incubation was continued overnight (about 14–16 hr) at 37° C. and the plates were visually inspected for the presence of the insoluble blue precipitate a product of the GUS enzyme acting on the X-Gluc substrate. Tissues derived from non-transformed plants or transformed plants not displaying sense suppression will show the presence of a blue precipitate indicative of GUS activity while tissue derived from plants in the suppressed state will show no or comparatively little blue precipitate.

The intensity of GUS staining, on a 0–10 scale, is shown in Table 1. Zero indicates no detectable blue deposition, and 10 indicates blue deposition continuously around the rim of the explant disk. A control plasmid that lacks nucleic acid sequences present in the transgene (i.e., pPO7113) resulted in a similar amount of GUS expression for both control and plasmid-containing plants. Plants in which a fragment of the transgene is present within the plasmid (i.e., pPO7110) exhibited a marked reduction in GUS expression relative to control plants that did not contain the plasmid.

Example 3
Preculture to Improve DNA Delivery

Explants from tomato plants of the varieties 1345 and 91103 were prepared as described in Example 2. Strawberry plants which were continuously cultured in axenic conditions in vitro are used as a source of leaf explants. No ethanol dip or other form of surface sterilization was done on the strawberry leaves. Explants were precultured on the same basic medium used for cocultivation in Example 2, except that the hormone combinations listed in the table were used. This preculture step was carried out under lights at 28° C. for 4 days.

Three different concentrations of acetyosyringone were used in the preculture medium, 100 $\mu$M, 250 $\mu$M and 1000 $\mu$M. Results with these concentrations are presented in Table 1.

Preparation of the Agrobacterium inoculum and inoculation and cocultivation were performed essentially as described in Example 2, except that the cocultivation step were done on the same medium as the preculture step by placing the explants back on the same preculture petri dish that they are taken from.

GUS assays were performed essentially as described in Example 2.

The data for tomato, using a SSR for the ACC-synthase transgene present in 1345 (i.e., pPO7110), indicates that the amount of SSR delivered to plant cells can be modified by altering plant growth regulator content in the incubation medium. In all cases, the expression of the SSR is lower in the suppressant than in the control.

The strawberry data indicate that the best medium composition for expression of a non-suppressed reporter (i.e., for DNA delivery) differs for different plants (cf. tomato line 91103).

TABLE 1

GUS Assay Results

|  | 1345 tomato | control tomato | strawberry |
|---|---|---|---|
| no hormones | 0,0,0,0 (0) | 0,0,0,0 (0) | 0,0,0,0 (0) |
| 1 mg/l 2,4-D | 2,2,3 (2.3) | 3,4,7,8 (5.5) | 0,0,0,0 (0) |
| 1 mg/l IAA | 0,4,4,6 (4.7) | 5,8,9,9 (7.8) | 0,0,0,0 (0) |
| 1 mg/l NAA | 0,0,0,1 (0.3) | 0,1,3,3 (1.8) | 0,0,0,0 (0) |
| 3 mg/l NAA | 0,1,2,4 (1.8) | 3,6,6,6 (5.25) | 0,0,0,1 (0.3) |
| 2,4D + 1 Zea | 0,0,0,1 (0.3) | 0,0,0,0 (0) | 1,2,6,8 (4.3) |
| IAA + 1 Zeatin | 0,0,0,0 (0) | 0,0,0,3 (0.8) | 2,3,5,7 (4.3) |
| 1 NAA + Z | 1,2,3,4 (2.5) | 3,4,10 (5.7) | 7,8,8,9 (8) |
| 3 NAA + Z | 0,0,0,2 (0.5) | 0,0,2,2, (1) | 7,8,9,9 (8.3) |
| vac 100AS | 0,0,0,0 (0) | 0,0,0,0 (0) | 0,0,0,0 (0) |
| vac 250AS | 0,0,0,0 (0) | 0,0,0,0 (0) | 0,0,0,0 (0) |
| vac 1000AS | 0,0,0,0 (0) | 0,0,1,2 (0.8) | 0,0,0,0 (0) |

The numbers represent a visual rating on a scale of 1 to 10. The number and size of the spots were both considered in giving the rating. The size of spots in 1345 tomato was consistently larger than the size of spots in 91103.

Example 4
Strawberry Cell Suppression.
Plant Population

A cell coding sequence of 1.53 kbp (Harpster et al., *Plant Mol. Biol.*, 33, 45–57, 1997) was engineered for expression using the SpMas promoter (Ni et al., *Plant J.*, 7, 661–76, 1995; construct number 5) and a nos 3' terminator sequence. This chimeric gene was cloned into a binary vector containing an acetolactate synthase gene that confers resistance to chlorsulfuron on plant cells, and introduced into strawberry cv. Chandler using *Agrobacterium tumefaciens*-mediated DNA delivery. Nearly 200 independent transgenic lines were obtained.

Visual Silencing Assay

One hundred seventy-eight of the cell transgenic lines were scored for suppression using the visual silencing assay to distinguish expression obtained with the SSR and NSR chimeric genes. The SSR chimeric gene was constructed using the cell coding sequence fragment of 1.53 kbp. This fragment was inserted in the 3' region of plasmid pPO7086 to provide an SSR with respect to strawberry cell sequences.

The visual assay was performed as described in Example 2 with the following modifications. Leaf explants of strawberry plants growing in vitro were used for the visual assay. 2–3 leaves were removed from plants, cut into strips, and divided into 2 groups, one of which was cocultivated with the SSR and one with NSR. The cocultivation medium is MS salts, B5 vitamins, 2% w/v glucose, 3 mM MES buffer, 0.8% w/v agar, 100 $\mu$M acetosyringone, 3 mg/1 NAA and 1 mg zeatin. The hormone conditions were those defined in Example 3.

To visualize GUS staining, leaf explants were cleared using ethanol washes. A plant was considered to be suppressed for cell when the NSR cocultivation yielded significant GUS staining around the cut surface while the SSR cocultivation yielded little or no GUS spots in any of the explant cut surfaces. Plants in which a significant number of GUS spots were observed on the cut surface with the SSR, but with which the SSR treatment had distinctly fewer GUS spots than the NSR treatment, was considered possibly suppressed. The assay was performed on two occasions, with the second assay performed approximately 6 weeks after the first. Only plants which were scored as suppressed on each assay, or as suppressed in one assay and possibly suppressed in a second were considered suppressed for further analysis.

Evaluation of Fruit Cell RNA Suppression

A clone of the plant assayed as described above was carried on and daughter plants were derived from that plant in a high elevation strawberry nursery. Several daughter plants were selected and grown to produce fruit in a greenhouse located in Brentwood, Calif. Fruit of individual plants (21 of which had been scored as suppressed, 18 of which had been scored an non-suppressed, and 7 of which were controls), was harvested at full ripeness, as judged by fruit color, and RNA was isolated using standard methods. Northern hybridization was done using a cell probe labelled using random priming. The blots were exposed for either 4 hours or 3 days. The results in Table 2 and Table 3 were obtained using a short exposure, as cell is a highly expressed gene in ripening fruit tissue. The RNA levels were scored using a visual scale, using 5 as the maximum detected level, and 0 as undetectable. For most samples, duplicate lanes were run to evaluate reproducibility.

A range of cell fruit expression levels was obtained both within the non-suppressed and suppressed populations (Table 2 and Table 3, respectively). Control plants gave expression levels of 4 to 5. Significant variation in visually detectable hybridization level was found with duplicates from some plants. The average RNA level was reduced in the population scored as suppressed using the visual silencing assay compared with the population scored as non-suppressed. The only three transgenic plants in which cell expression in fruit was reduced to an undetectable level even in a long exposure of the Northern blot were identified by the visual suppression sensitive assay.

TABLE 2

RNA levels in transgenic population scored as not suppressed with visual silencing assay.

| LINE # | RNA SCORE 1 | RNA SCORE 2 | RNA AVERAGE |
|---|---|---|---|
| 31 | 1.5 | 4 | 2.75 |
| 76 | 5 | 3 | 4 |
| 101 | 2.5 | 0.5 | 1.5 |
| 114 | 4 | 5 | 4.5 |
| 130 | 3 | 3 | 3 |
| 145 | 3.5 | 1 | 2.25 |
| 147 | 4 | 3 | 3.5 |
| 151 | 5 | 4 | 4.5 |
| 181 | 5 | 2 | 3.5 |
| 186 | 1 | 1 | 1 |
| 187 | 2 | 3 | 2.5 |
| 209 | 4 | 4 | 4 |
| 227 | 3.5 | 3 | 3.25 |
| 243 | 5 | 5 | 5 |
| 277 | 3 |  | 3 |
| 302 | 5 |  | 5 |
| 301 | 1 | 1.5 | 1.25 |
|  |  |  | Avg = 3.21 |

TABLE 3

RNA levels in transgenic population scored as suppressed in visual silencing assay.

| LINE # | RNA SCORE 1 | RNA SCORE 2 | RNA AVERAGE |
|---|---|---|---|
| 13 | 0 |  | 0 |
| 93 | 1 | 1.5 | 1.25 |
| 103 | 2.5 |  | 2.5 |
| 108 | 2 | 2 | 2 |
| 109 | 1 | 1 | 1 |
| 121 | 5 | 5 | 5 |
| 226 | 0 | 0 | 0 |
| 230 | 0 |  | 0 |
| 238 | 5 | 5 | 5 |
| 247 | 2 | 1.5 | 1.75 |
| 248 | 1.5 | 1 | 1.25 |
| 256 | 2.5 | 2.5 | 2.5 |
| 258 | 1 | 5 | 3 |
| 259 | 4 | 4 | 4 |
| 261 | 1.5 |  | 1.5 |
| 262 | 4.5 | 1 | 2.75 |
| 268 | 1.5 |  | 1.5 |
| 276 | 2 | 2 | 2 |
| 285 | 5 | 5 | 5 |
| 292 | 5 | 5 | 5 |
| 295 | 3 | 5 | 4 |
|  |  |  | avg = 2.43 |

Example 5

Quantitative Assay For Post-transcriptional Gene Silencing

The suppression sensitive reporter assay is useful for quantifying the amount of post-transcriptional gene silencing. This is done using a second reporter, a non-suppressible reporter (NSR), to control for the amount of DNA delivery. The assay can be performed using either *Agrobacterium tumefaciens* to deliver both reporter genes, either as a single T-DNA or in distinct T-DNA molecules. In one example, a LUC-int SSR is created, using the target coding sequence in the 3' non-translated region of the LUC-int gene. For the non-suppressible reporter, a second LUC-int gene is created using a different LUC sequence that can be assayed independently from the first. For example, the second luciferase is from *Renilla reniformis*, with firefly luciferase assayed first in extracts, followed by inactivation of the firefly luciferase and assay of the Renilla luciferase. These genes are available commercially from Promega (Madison, Wis.). The luciferase assays are rapid assays to facilitate rapid screening of transgenic populations.

Using Agrobacterium cocultivation, the SSR and the NSR are introduced into strawberry leaf tissue at the same time. After 2–3 days incubation, a cell-free extract is prepared from the leaf tissue for assay of the two luciferase enzymes. The NSR activity is used to normalize the SSR activity, with the percentage of suppression then being reported as:

$$\% \text{ Suppression} = 100 \times \frac{SSR_{act}(\text{control})/NSR_{act}(\text{control}) - SSR_{act}(\text{experimental})/NSR_{act}(\text{experimental})}{SSR_{act}(\text{control})/NSR_{act}(\text{control})}$$

For example, if the control ratio were 0.25, and the experimental ratio were the same, then the extent of suppression would be 0%. If the experimental ratio were 0.1 or 0.01, with a control ratio of 0.25, then the extent of suppresion would be 60% or 96%.

One important use of the quantitative assay is with biolistic delivery of DNA. The quantitative assay can reduce the sensitivity of the assay to partial silencing. If a relatively small amount of SSR transcript is made in comparison with the degradative capacity of the PTGS mechanism, then all the SSR transcript could be degraded even when only a small extent of suppression is induced. Using the equation indicated above, plants with little phenotypic suppression might be quantified as highly suppressed. Using a very strong promoter, or using biolistics with large amounts of DNA per particle, to provide, more of the SSR transcript yields a quantitative assay with a useful range.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for detecting post-transcriptional silencing of a chosen gene in a plant cell, the method comprising:

introducing into the plant a nucleic acid comprising a promoter operably linked to a suppression-sensitive reporter (SSR) gene which comprises a) a reporter coding sequence, and b) a targeting nucleotide sequence wherein such targeting nucleotide sequence is at least 80% identical to the chosen gene, wherein the reporter coding sequence and the targeting nucleotide sequence are transcribed as a single mRNA transcript; and determining the level of expression of the reporter coding sequence to determine whether post-transcriptional gene silencing of the chosen gene has occurred.

2. The method of claim 1, wherein the chosen gene is an endogenous gene.

3. The method of claim 2, wherein the plant cell comprises a transgene which produces a transcript that is at least 80% identical to the endogenous gene.

4. The method of claim 1, wherein the chosen gene is a transgene.

5. The method of claim 4, wherein the targeting nucleotide sequence is at least 95% identical to a nucleotide sequence present in a plant virus.

6. The method of claim 1, wherein the post-transcriptional gene silencing is selected from the group consisting of sense suppression and antisense suppression.

7. The method of claim 1, wherein the plant cell is contained in a plant.

8. The method of claim 1, wherein the promoter is a constitutive promoter.

9. The method of claim 8, wherein the promoter is a cauliflower mosaic virus 35S promoter or a figwort mosaic virus promoter.

10. The method of claim 8, wherein the promoter is a heterologous promoter with respect to the targeting nucleotide sequence.

11. The method of claim 1, wherein the introducing is by cocultivating the plant cell with Agrobacterium cells that comprise a nucleic acid which comprises the SSR gene flanked by functional T-DNA borders.

12. The method of claim 11, further comprising, prior to said introducing step, excising a plant cell from a plant.

13. The method of claim 12, further comprising, after said excising step, preculturing said cell on artificial medium, wherein said cell is contained in a plant tissue.

14. The method of claim 1, wherein the SSR gene is incapable of expression in bacterial cells.

15. The method of claim 14, wherein the SSR gene further comprises an intron.

16. The method of claim 14, wherein the SSR gene further comprises a bacterial transcription termination signal at the 3' end of the targeting nucleotide sequence.

17. The method of claim 1, wherein the targeting nucleotide sequence is located in a 3' untranslated region of the reporter coding sequence.

18. The method of claim 1, wherein the reporter coding sequence encodes a reporter moiety selected from the group consisting of β-glucuronidase (uidA), luciferase, green fluorescent protein (GFP), and chloramphenicol acetyltransferase (CAT).

19. The method of claim 18, wherein the reporter moiety is an *Escherichia coli* β-glucuronidase.

20. The method of claim 1, wherein the expression of the SSR gene is detected quantitatively.

21. The method of claim 1, wherein the method further comprises introducing into the plant cell a non-suppression reporter (NSR) gene which comprises a second reporter coding sequence which is different from the reporter coding sequence included in the SSR gene and lacks a targeting nucleotide sequence, and determining the level of expression of both the reporter coding sequence and the non-suppression sensitive reporter to determine whether post-transcriptional gene silencing of the chosen gene has occurred.

22. The method of claim 21, wherein the second reporter coding sequence encodes a reporter moiety selected from the group consisting of β-glucuronidase (uidA), luciferase, green fluorescent protein (GFP), and chloramphenicol acetyl transferase (CAT).

23. The method of claim 21, wherein the introducing is by cocultivating the plant cell with Agrobacterium cells that comprise a nucleic acid which comprises the NSR gene flanked by functional T-DNA borders.

24. The method of claim 23, wherein the SSR gene is flanked by the same functional T-DNA borders as is the NSR gene.

25. The method of claim 23, wherein the SSR gene and the NSR gene are flanked by two separate sets of functional T-DNA borders.

26. The method of claim 25, wherein each of the two sets of function T-DNA borders is present in a single Agrobacterium strain.

27. A method for detecting transgene-induced post-transcriptional silencing of an endogenous gene in a plant cell, the method comprising:

introducing into the plant cell a nucleic acid comprising a promoter operably linked to a suppression-sensitive reporter (SSR) gene which comprises a) a reporter coding sequence, and b) a targeting nucleotide sequence wherein such targeting nucleotide sequence is at least 80% identical to the endogenous gene, wherein the reporter coding sequence and the targeting nucleotide sequence are transcribed as a single mRNA transcript; and determining the level of expression of the reporter coding sequence to determine whether post-transcriptional silencing of the endogenous gene has occurred.

28. A method for assaying a plant to determine whether a chosen gene is post-transcriptionally silenced, the method comprising:

introducing into cells obtained from the plant a nucleic acid comprising a promoter operably linked to a suppression-sensitive reporter (SSR) gene which comprises a) a reporter coding sequence, and b) a targeting nucleotide sequence that is at least 80% identical to the chosen gene, wherein the reporter coding sequence and the targeting nucleotide sequence are transcribed as a single mRNA transcript; and determining the level of expression of the reporter coding sequence gene to determine whether post-transcriptional silencing of the chosen gene has occurred.

29. The method of claim 28, wherein the cells comprise a transgene that is at least 95% identical to the chosen gene.

30. The method of claim 28, wherein the method further comprises introducing into the cells a non-suppression sensitive reporter (NSR) gene which comprises a reporter gene that encodes a reporter moiety which is different from the reporter moiety encoded by the SSR gene, and determining the level of expression of both the SSR gene and the NSR gene, wherein a decreased level of SSR gene expression relative to NSR gene expression is indicative of post-transcriptional gene silencing.

31. A method of identifying plant cells that use post-transcriptional gene silencing to resist infection by plant virus, the method comprising:

introducing into the plant cells a nucleic acid comprising a promoter operably linked to a suppression-sensitive reporter (SSR) gene which comprises a) a reporter coding sequence, and b) a targeting nucleotide sequence wherein such targeting nucleotide sequence is at least 80% identical to a nucleotide sequence obtained from the plant virus, wherein the reporter coding sequence and the targeting nucleotide sequence are transcribed as a single mRNA transcript; and determining the level of expression of the reporter coding sequence, wherein a reduction in reporter coding sequence expression is indicative of cells that are resistant to infection by the plant virus.

32. The method of claim 31, wherein the plant virus is selected from the group consisting of potato virus Y and related potyviruses, tobacco etch virus, and tobacco vein mottling virus.

* * * * *

SEQUENCE LISTING

<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:NC-201
      oligonucleotide

<400> SEQUENCE: 1
ctagtaggat ccggtaccat cgattctaga c                                31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:NC-202
      oligonucleotide

<400> SEQUENCE: 2
ctaggtctag aatcgatggt accggatcct a                                31

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:NC-190
      oligonucleotide primer

<400> SEQUENCE: 3
cggccatggg tttagcagaa aatcagc                                     27

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:NC-191
      oligonucleotide primer

<400> SEQUENCE: 4
cggccatgga acaaactcga aaccaacctg g                                31